United States Patent [19]

Haymore et al.

[11] Patent Number: 5,115,102
[45] Date of Patent: May 19, 1992

[54] VARIANT PROTEINS AND POLYPEPTIDES POSSESSING ENHANCED AFFINITY FOR IMMOBILIZED-METAL AFFINITY MATRICES

[75] Inventors: Barry L. Haymore, Creve Coeur; Gary S. Bild, Chesterfield; Gwen G. Krivi, St. Louis, all of Mo.

[73] Assignee: Monsanto Company, St. Louis, Mo.

[21] Appl. No.: 383,778

[22] Filed: Jul. 21, 1989

[51] Int. Cl.⁵ .................. C07K 3/18; C07K 15/00; C12N 15/09
[52] U.S. Cl. .................. 530/399; 530/350; 530/413; 435/69.1
[58] Field of Search .................. 530/350, 399, 413; 435/68, 69.1

[56] References Cited

U.S. PATENT DOCUMENTS 4,569,794 2/1986 Smith et al. .................. 530/344

FOREIGN PATENT DOCUMENTS

184355A2 6/1986 European Pat. Off. .

OTHER PUBLICATIONS

Scopes, R. K., 1987, *Protein Purification: Principles and Practices*, Springer Verlag, New York, pp. 234-235.
Seeburg et al., 1983, *DNA* 2(1):37-45.
Smith et al., J. Bio. Chem., 263 (15), 7211 (1988).
Affinity Chromatography and Related Techniques, Gribnau et al., Editors, Elsevier Scientific Publishing Co., Amsterdam (1982).
Sulkowski, Texas Rep. on Biol. and Med., 41, 234 (1981).
Hochuli et al., Biotechnology, 6, 1321 (1988).
Hochuli, J. Chrom., 444, 293 (1988).
Sulkowski, Trends in Biotechnology, 3, 1 (1985).
Hemdan et al., Proc. Natl. Acad. Sci., 86, 1811 (1989).

Primary Examiner—Margaret Moskowitz
Assistant Examiner—Keith C. Farman
Attorney, Agent, or Firm—Charles E. Smith; James W. Williams, Jr.; James C. Bolding

[57] ABSTRACT

The present invention is directed at variant proteins and polypeptides having an enhanced affinity, i.e., greater binding strength, for immobilized-metal affinity resins and resides in engineering one or more specific metal-chelating amino acid sequences into a protein or polypeptide, the specific sequence depending on the metal-binding amino acids utilized and the secondary structure associated with the portion of the protein or polypeptide to include such sequence.

13 Claims, 2 Drawing Sheets

A = INJECTION PEAK
B = NATIVE SOMATOMEDIN C.
C = UNFOLDED VARIANT (SULFUR-CAPPED-HEXATHIOSULFONATE DERIVATIVE).
D = MISFOLDED SOMATOMEDIN C VARIANT.
E = PROPERLY FOLDED SOMATOMEDIN C VARIANT.
    NOT SHOWN IS THE UNFOLDED NATIVE IGF1 HEXATHIOSULFONATE WHICH DOESN'T BIND TO THE METAL COLUMN.

A = INJECTION PEAK
B = NATIVE SOMATOMEDIN C.
C = UNFOLDED VARIANT (SULFUR-CAPPED-HEXATHIOSULFONATE DERIVATIVE).
D = MISFOLDED SOMATOMEDIN C VARIANT.
E = PROPERLY FOLDED SOMATOMEDIN C VARIANT.
   NOT SHOWN IS THE UNFOLDED NATIVE IGF1 HEXATHIOSULFONATE
   WHICH DOESN'T BIND TO THE METAL COLUMN.

VARIANT PROTEINS AND POLYPEPTIDES POSSESSING ENHANCED AFFINITY FOR IMMOBILIZED-METAL AFFINITY MATRICES

BACKGROUND OF THE INVENTION

1. Field of the Invention

The present invention relates to variant proteins and polypeptides which manifest enhanced affinity for immobilized-metal affinity matrices. More particularly, the present invention relates to proteins and polypeptides having at least one metal-chelating amino acid sequence engineered thereinto.

2. Prior Art

When recombinant proteins or polypeptides are expressed in bacterial cells and subsequently grown in fermentation tanks, there remains the problem of recovering the desired product in pure form. Immobilized-metal affinity chromatography or ligand exchange chromatography is a well known technique for amino acid and protein purification. F. Helfferich, Nature 189, p. 1001 (1961); H. F. Walton et al, Recent Developments in Separation Science, Vol. VI, Chapter 5 1981. Porath et al, Nature (London), 258, p. 598 (1975); Biochemistry, 22, p. 1625 (1975) and Sulkowski, Trends in Biotechnology, 3, p. 1 (1985), have shown that this technique is well suited for selective fractionation of native proteins according to their content of exposed histidine residues. The chelating ligands such as iminodiacetic acid were bound covalently to oxirane-activated agarose, and the resulting gels were charged with metal ions such as $Cu^{2+}$, $Zn^{2+}$, $Ni^{2+}$ or $Co^{2+}$. Such resins have since been utilized for purification of several native peptides and proteins. See, for example, Nilsson et al, Embo J. 4, p. 1075 (1985).

It was desirable, however, that a method be developed for purifying all recombinant proteins and polypeptides, not just those which inherently contain one or more exposed histidine side chains or residues. To this end, hybrid proteins were developed wherein the coding sequence of a protein of interest was fused with the coding sequence of a small histidine-containing peptide. The coding sequence of the affinity peptide is fused to the protein of interest along with the sequence of a specific cleavage site. Such fusion proteins can then be purified by taking advantage of the binding of the histidine-containing peptide, or affinity tail, to the affinity matrix. After purification of the fusion protein, the affinity tail is split off at the designed cleavage site, which is a very difficult and expensive procedure, and the protein of interest is purified in a final step. See, for example, Smith et al Biol. Chem. 263, 7211 (1988). In general this technique is not suited for separating the desired protein from other proteins which inherently include one or more metal-binding amino acids, particularly since many protein impurities are likely to contain multiple exposed histidines. However, if the affinity tail contains 6-8 or more histidines, this method can be useful. See Hochuli et al, Biotechnology, 6, 1321 (1988).

Thus, it would be desirable to have a method for protein and polypeptide purification which is applicable to all recombinant proteins and polypeptides and which is effective in separating the desired protein from other proteins which inherently include one or more metal-binding amino acids.

It has now been discovered that the binding of a protein or polypeptide to an immobilized-metal affinity matrix can be enhanced to an extent which is significantly greater than that of native proteins and polypeptides which inherently include one or more metal-binding amino acids as well as fusion proteins and polypeptides. Such enhanced affinity is effected by engineering into such protein or polypeptide a metal-chelating amino acid sequence within the primary sequence thereof and at a specific segment of the secondary structure.

SUMMARY OF THE INVENTION

The present invention is directed at variant proteins and polypeptides having an enhanced affinity, i.e., greater binding strength, for metal affinity matrices. The present invention resides in engineering, preferably utilizing recombinant DNA methodologies, one or more specific metal-chelating amino acids into a protein or polypeptide, the specific sequence depending on the particular metal-binding amino acids contained in the sequence and the secondary structure associated with the portion of the protein or polypeptide which will include such sequence.

DETAILED DESCRIPTION OF THE INVENTION

Figure 1:
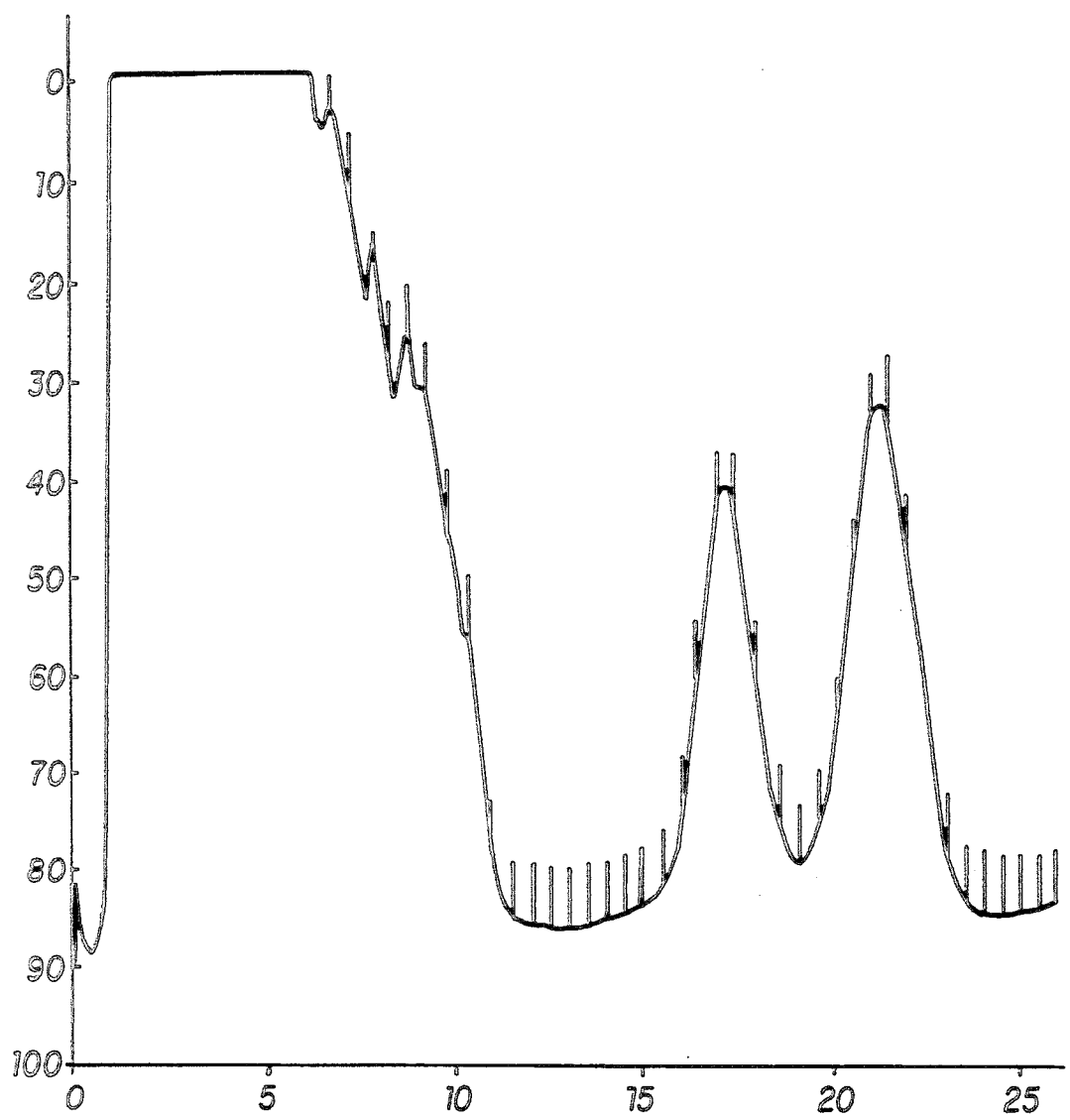
FIG. 1 illustrates the elution profile of a crude refold mixture of $A_{-1}H_8H_{12}$ insulin-like growth factor-1 (IGF1) modified according to the teachings of the present invention.

As utilized herein, the term "metal-chelating amino acid sequence" means a sequence of amino acids which includes at least two metal-binding amino acids stereochemically arranged such that a simultaneous two-site attachment may be formed with an immobilized metal. Where a sequence of amino acids includes a metal-binding amino acid, such amino acid will form a coordination bond with the immobilized metal of the immobilized-metal affinity matrix, thereby resulting in a ternary "metal complex" (immobilizing ligand + metal + peptide). However, if such sequence includes two or more metal-binding amino acids which are properly oriented, simultaneous coordination with the transition metal by both amino acids results in a "metal chelate". Such chelation will result only when proper stereochemical factors and conformational constraints lead to favorable enthalphy and entropy effects. The present invention provides variant proteins and polypeptides which contain a metal-chelating amino acid sequence and, therefore, manifest enhanced affinity for resins.

The metal-chelating sequence can be represented by the formula: $-A-B_x-C_y-D_z-E-$ wherein A and E are independently metal-binding amino acids selected from the group consisting of histidine and aspartate provided that at least one of either A or E is histidine, B, C and D are amino acids, and x, y and z are integers from 0 to 3 depending on the secondary structure of the surface exposed portion of the protein or polypeptide molecule which includes the metal-chelating or sequence-containing site and the particular metal-binding amino acids utilized in the metal chelating sequence. The sum of x, y and z in combination with the secondary structure of the sequence-containing site determines whether the stereochemical requirements are met in order for A and E to simultaneously bind to the immobilized metal and thus form a chelate. Where the metal-binding amino acids are independently histidine or aspartate, and the metal-chelating sequence is to be engineered into an α-helical segment of the protein or polypeptide, x+y+z is equal to 3. Where such segment is a β-hairpin turn, x+y+z is equal to 2 and where such segment is a β-strand, x +y+z is equal to 1.

Where the native protein or polypeptide lacks an accessible or available metal-binding amino acid at the proper position, the entire sequence must be engineered into such protein or polypeptide at such position. However, where the protein or polypeptide includes an accessible metal-binding amino acid at the proper position, e.g., on an α-helix, only one additional metal-binding amino acid is required to be engineered into such protein or polypeptide in order to effect the proper sequence.

The proper position for placing the metal-binding amino acids is readily determined for those proteins and polypeptides with known structures. Where the structure has not been determined, the primary sequence can be determined by well known methods and the secondary structure can be usefully predicted as demonstrated below, utilizing methods well known in the art.

Proper positioning may be determined, for example, as defined below. Calculations are based on the following facts for a desired metal chelate: 1) that the donor atoms in the protein ligands are matched to the particular metal ion or metal complex; 2) that the two or more metal-binding atoms easily satisfy the specific geometric requirements of the metal; 3) that the chelating form of the protein ligand is conformationally constrained (relatively inflexible or rigid).

Of the natural amino acids, only the side chains of cysteine, histidine, aspartate and glutamate have significant binding strength in aqueous solutions for divalent first row transition metals at neutral pH. Thus,

*cys> his> >asp, glu>other amino acids*

For a cis disposition of ligands binding to $Cu^{2+}$ (similarly for $Ni^{2+}$, $VO^{2+}$ and $Zn^{2+}$), X-ray crystallographic data for metal complexes show that typical copper-nitrogen bonding parameters are Cu-N=1.98-2.02 Å and N—Cu—N=80°-100°. X-ray crystallographic data for proteins show three commonly observed secondary structural features: α-helices, β-strands and β-hairpin turns. These structured regions at least partially fulfill the requirement of conformational constraint. Typical conformational values for α-helices ($\phi=-57°$, $\psi=-47°$, $\omega=180°$), β-strands ($\phi=-139°$, $\psi=+135°$, $\omega=180°$) and β-hairpin turns (Type I', Type II') were used. Geometric searches of energetically acceptable sidechain conformations for his and asp residues were carried out to find which amino acid sequences coupled with corresponding secondary structures could provide a bidentate chelating site for $Cu^{2+}$ with the above distance and angular constraints. Only short range chelating interactions were considered; i.e., the number of intervening residues between the binding residues was 0 to 4. The results of the calculations are shown in the following table; (+) shows when chelation can occur and (−) show when chelation cannot occur. The nature of the intervening residues ("X") is relatively unimportant; the modeling demonstrated that the steric size, the hydropathicity and the charge of the sidechains of these residues play only minor or secondary roles in determining the strength of the metal-chelating peptide interactions.

| Sequence | α-Helix | β-Strand | β-Hairpin Turn |
|---|---|---|---|
| HH | − | − | − |
| HxH | − | + | − |
| HxxH | − | − | + |
| HxxxH | + | − | − |
| HxxxxH | − | − | − |
| DH | − | − | − |
| DxH | − | + | − |
| DxxH | − | − | + |
| DxxxH | + | − | − |
| DxxxxH | − | − | − |
| HD | − | − | − |
| HxD | − | + | − |
| HxxD | − | − | + |
| HxxxD | + | − | − |
| HxxxxD | − | − | − |

Once regions of regular secondary structure have been identified, it is necessary to determine which residues in these regions are sufficiently exposed on the surface of the protein so that they could easily bind to immobilized metals. The periodicity of the hydropathy over the region of interest was used as a guide in finding the exposed residues. Although a number of hydropathy scales have been defined, the one most useful in the present application is the scale based on the degree to which a particular amino acid residue is buried or exposed based upon proteins whose structures are determined by X-ray crystallography, see (Kideva et al, J. Protein Chem., 4, 23, (1985); Table III, property 4.

α-Helix For the entire helical region of interest, the hydropathic moment (direction and magnitude) was calculated using a pitch of 1% residues per 5 turns (100°/residue). If the hydropathic moment was sufficiently large ($>|0.3|$), the residues were then classified into three equally populated categories; exposed, buried and borderline.

β-Strand For the entire β-strand region of interest, the hydropathic moment was calculated using a pitch of 2 residues per turn (180°/residue). This is an easy calculation for β-structures because each residue is either "up" or "down". In this case, the residues were classified into two equally populated categories: exposed and buried.

β-Hairpin Turn Because these two-residue turns are supersecondary structures, there is little need for further calculations once the residues in the turn have been identified. The residues suited for metal chelation are the two residues on either side of the hairpin turn. These turns occur most frequently on exposed surfaces of proteins with the turn residues and adjacent residues exposed.

Having determined the proper position for placing the metal-binding amino acids, the variant proteins and polypeptides may be prepared according to techniques well-known to those skilled in the art. Such variants may include a single metal-chelating site as well as a plurality of such sites depending on the desired affinity for a particular immobilized metal resin.

The variant proteins and polypeptides of this invention may be prepared by chemical synthesis. However, because proteins and polypeptides possessing secondary structures are generally large molecules, it is preferred to prepare them by recombinant DNA technology. This can be done utilizing conventional means to construct a gene encoding the desired variant protein or polypeptide having the desired metal-chelating sequence in the proper position. A convenient method of constructing the variant proteins and polypeptides is by conventional oligonucleotide-directed site-specific mutagenesis of the starting gene. The mutated gene is then cloned into an appropriate vector which vector subsequently is utilized to transform a suitable expression host, such as bacteria (e.g., E. coli or Pseudomonas), yeast (e.g., S. cerevisae), or mammalian cells (e.g., C127 or CHO). The variant protein or polypeptide is then expressed in a conventional manner and recovered as described below.

The variant proteins and polypeptides thus produced will typically have only one to two modifications in the primary sequence. Such small modifications are expected to, and typically do, result in a variant protein or polypeptide which retains the biological properties of the native protein or polypeptide. Furthermore, such modifications are not expected to and do not typically affect the antigenic characteristics thereof.

are commonly referred to as "growth hormones". Native bovine and porcine somatotropins include histidine residues at positions 19, 21 and 169. $His_{19}$ and $His_{21}$ are both on α-helial segments and are exposed. $His_{21}$ is buried. Metal-binding amino acids were engineered into bovine and porcine somatotropins, according to the following procedure, to produce variant somatotropins having a metal-chelating site. Enhanced affinity for immobilized-metal affinity matrices is shown in Table 1 for the variants produced according to this invention.

Variant Genes

The residues at the positions indicated in Table 1 of the BGH and PGH structural genes described in Seeburg et al., DNA, 2, p. 37, (1983), are changed by oligonucleotide-directed, site-specific mutagenesis. Oligonucleotide mutagenesis primers are synthesized on an Applied Biosystems DNA Synthesizer in accordance with the procedures set forth by the manufacturer, Applied Biosystems, Inc. (Foster City, Calif.). The sequence of the mutagenesis primers are:

| | |
|---|---|
| BST | TTTGAAGGTGTCA<u>T</u>GAGCCAGCTGAT |
| BST | TGCCCAGCA<u>T</u>GGGGGGTG |
| BST | AAGATGCTGAGCA<u>T</u>GAAGAACAGCG |
| BST | GTCGTCACT<u>A</u>TGCATGTTTGTG |
| ABST | TGCCCAGCA<u>T</u>GGGGGGTG |
| ABST | GTCGTCACT<u>A</u>TGCATGTTTGTG |
| BST | CTGAGCACGA<u>T</u>GAACAGCGT |
| BST | GTTGGTGAAGACA<u>T</u>GGCTGAGGAACTG |
| ABST | CTGAGCACGA<u>T</u>GAACAGCGT |
| ABST | CTGAGCACGA<u>T</u>GAACAGCGT |
| PST | GCTAACGCTGTTCA<u>T</u>CGGGCCCAGCAC |
| ABST | ATGAACAGCGTTA<u>T</u>GGAATAGACCAGA |
| ABST | ACCGTAGTT<u>G</u>T<u>G</u>GAGCAGCGCGT<u>G</u>GTCACTGCG |
| ABST | GGTGCGCTCAAA<u>A</u>T<u>G</u>TTTGAAGGTGT<u>G</u>AGCAGCCAGCTG |
| ABST | ATGCAGGTCCTT<u>G</u>TGGAAGCAGGAGA |
| ABST | GACCCTCAGGTA<u>GT</u>GCTCCGTCTTATG |
| PST | AAGAAGGACCTG<u>A</u>GCAAGGCTGAGACA |

DESCRIPTION OF PREFERRED EMBODIMENTS

EXAMPLE 1

VARIANT SOMATOTROPIN

This example illustrates the present invention as applied to a protein, namely, somatotropin which has two available metal-binding amino acids, wherein at least one additional metal-binding amino acid is engineered thereinto to effect a metal-chelating sequence. This example also illustrates application of the present invention to a protein wherein the structure is known.

Somatotropins are naturally occurring proteins found in animals and, because of their effect on animal growth The underlining indicates the codon which changes the native residue to the desired residue.

The BGH gene used as template DNA consisted of the BGH gene described in Seeberg et al cloned into M13mp18 vector (Bethesda Research Laboratory, Gaithersburg, Md.) as a EcoRI/HindIII fragment. Also used as a template is the N-alanyl, valine (126) BGH gene described in European Patent Application No. 193,515, published Sept. 3, 1986, cloned into the M13mp18 vector as an EcoRI/HindIII fragment. The PGH gene used as template DNA as the N-alanyl PGH gene described in European Patent Application No. 193,515 cloned into the M13mp19 vector (BRL) as an EcoRI/HindIII fragment. Before the mutagenesis of the PGH gene at the desired position, the 5' end of the gene was mutagenized to create an NcoI site in order to facilitate later subcloning into the expression plasmid. The primer used for this mutagenesis was synthesized as those above and has the structure of

5'-CAGTGAATTCTCCATGGCCTTCCCAGC-3

The mutagenesis procedure for the NcoI site addition is described by Kunkel, (Proc. Natl. Acad. Sci., 82, p. 422 [1985]). All restriction enzymes and modifying enzymes (T4 DNA ligase and polynucleotide kinase) are purchased from New England Biolabs (Beverly, Mass.) and used according to the manufacturer's directions.

The mutagenesis is carried out using the Amersham (Arlington Heights, IL) Oligonucleotide-directed in vitro Mutagenesis System, according to instructions of the manufacturer. Following mutagenesis, positive mutant genes are identified by DNA sequence analysis using the Sequenase TM DNA sequencing system of United States Biochemical Corporation (Cleveland, Ohio) according to the manufacturer's instructions. The mutated genes are then cloned as EcoRI/HindIII fragments into E. coli expression vector pMON2534. Plasmid pMON2534 is a derivative of pBGH$_{ex-1}$ (Seeburg et al) with a tandem lacUV5 promoter inserted at the HindIII site of pBGH$_{ex-1}$ as a transcription terminator. The sequence of the tandem lacUV5 promoter as an EcoRI fragment is described in Bogosian et al, (Nucleic Acid Research, 15, 7185 [1987]). The EcoRI fragment is converted to a HindIII fragment by filling in the EcoRI overhangs and attaching HindIII linkers. These manipulations yield the sequences which are found at the ends of the HindIII fragment. At the upstream end, the HindIII linker (AAGCTT) ligated to the filled-in EcoRI end (AATTCT...) produces the sequence AAGCTTAATTCT...; the CT at positions 11 and 12 represents the right half of the AluI site from the original lacUV5 promoter fragment. At the downstream end, the squence produced is ..AGAATTAAGCTT; the AG at positions $-12$ and $-11$ represents the left half of the AluI site from the original lacUV5 promoter fragment. In addition, pMON2534 has the EcoRI site at the 5' terminus of the ptrp fragment of pBGH$_{ex-1}$ and the HindIII site at the 3' terminus of the tandem lacUV5 promoter/operator fragment removed by digestion of the overhand EcoRI and HindIII ends using S1 nuclease and blunt-ended ligation with T$_4$ DNA ligase. Plasmid pMON5585 is a pBR327 plasmid containing E. coli recA promoter, a G10L sequence, and T$_7$ transcription termination sequence as described in European Patent Application Number 241, 446, published Oct. 14, 1987. The mutant BGH and PGH genes cloned into the expression plasmids are inserted into E. coli strain W3110 (ATCC #39936).

Cell Lysis and Isolation of Inclusion Bodies

After thawing an appropriate amount of frozen cell paste at 5° C., 120 g of the cell paste was carefully suspended in 480 mL cold water using an Ultra Turrax stirrer. The chilled cell suspension was passed 4 times through a pre-cooled Manton Gaulin homogenizer set at 6000-8000 psi pressure. The resulting suspension of lysed cells was subjected to ultracentrifugation at 50,000 ×g (25,000 rpm in 45TI rotor) for 35 minutes using a Beckman Model L8 centrifuge. The clear supernatant liquid was poured off, and the remaining brownish pellet was vigorously washed with a small stream of water in order to remove the top slimy layer of unwanted cell debris. The pellet was resuspended in water and subjected a second time to ultracentrifugation and washing. The remaining material was mechanically scraped out of the centrifuge tubes and combined to yield 4.7 g of damp inclusion bodies which were stored at $-80°$ C. for future use.

Oxidation and Folding of Somatotropin

A 4.0 g mass of inclusion bodies was suspended in 300 mL cold water using an Ultra Turrax stirrer. The volume of the suspension was increased to 375 mL by the addition of more water. Then 425 mL cold, freshly prepared, deionized urea solution (7.5 M) was added to the suspension to yield a mixture about 4M in urea. With good stirring, the pH was adjusted to 11.3 by the dropwise addition of 2.5 M NaOH solution. During the NaOH addition, most of the suspended inclusion bodies dissolved, yielding a light yellow solution. This solution was vigorously stirred in an open container at 5° C. for 48-72 hours in order to effect the refolding of the desired protein. On several occasions cysteine (9.7 mg, 0.1 mM) was added to the mixture which shortened the refolding time by about half. In order to remove residual insolubles, the refolded mixture was subjected to ultracentrifugation at 50,000 ×g (25,000 rpm in Beckman 45TI rotor). The clear yellow supernatant liquid was decanted off and then prepared for purification or stored at $-20°$ C. A 2 ml sample of the crude refold mixture was tested on a small copper-loaded metal-affinity column to determine if the binding was strong enough to be useful. If so, a preparative metal-affinity column was used for purification; otherwise, ion-exchange chromatography was used.

Preparation of Functionalized Resin

Trisacryl GF2000M was repeatedly washed with distilled water to remove all buffers and preservatives and then dried by suction. About 100 g ($\sim$100 mL) of this slightly damp matrix was suspended in a solution containing 80 mL diglyme and 100 mL freshly prepared 1.4 M NaOH solution. Finally, 100 mL diethyleneglycol diglycidylether was added, and the mixture was gently stirred at 35° C. for 16 hours. Purified diethyleneglycol diglycidylether was prepared by the literature method of Gu, Ideda and Okahara (Synthesis, 649, [1985]). The activated matrix was washed with diglyme/H$_2$(50/50) and then repeatedly washed with distilled water to remove the excess epoxide and base. The washed, suction-dried matrix was shown to have 70 micromoles active epoxide groups per mL resin. The activated resin was stored at 4° C. and generally used within 24 hours of preparation.

Immobilization of Chelate

The activated Triascryl was washed with distilled water and dried by suction. About 100 g ($\sim$100 mL) of this activated gel was suspended in 100 mL 1.0 M Na$_2$NH(CH$_2$CO)$_2$ solution, which was adjusted to pH=10.5-11.0. This mixture was gently stirred at 65° C. for 24 hours and then repeatedly washed with distilled water to remove excess ligand. The functionalized resin was stored in ethanol/water (25/75 v/v) at 4° C. until ready for use. Titration with thiosulfate showed the absence of epoxide groups, so capping with ethanolamine was deemed unnecessary. Ten milliliters of suction-dried gel was saturated with excess 50 mM Cu(-

ClO$_4$)$_2$ and then carefully washed with 100 mL distilled water, 100 mL 50 mM imidazole (pH=7.0) and finally 100 mL H$_2$O. Then the bound copper was removed with an excess of 50 mM Na$_2$H$_2$EDTA (pH=7.0). Using standardized copper-EDTA solutions for comparison, the total copper content was photometrically determined to be 0.43 millimoles.

Elution Protocol for Metal-Affinity Column

A glass column (2.2×21 cm, 80 mL) was packed with carefully washed IDA-Trisacryl gel and then charged with 400 mL 50 mM Cu(ClO$_4$)$_2$ (pH=4.5). The functionalized gel nearly quantitatively absorbed the copper ions. This copper column was washed with 100 mM NaCl, and then it was equilibrated with the release buffer (100 mM N$_\alpha$-acetylhistidine, 500 mM NaCl, 50 mM NaH$_2$PO$_4$, pH=7.0) and finally equilibrated with the loading buffer (1 mM N$_\alpha$-acetylhisti 500 mM NaCl, 50 mM NaH$_2$PO$_4$, pH=7.0). The filtered crude refold mixture (~800 mL) was pumped onto the column at 5 mL/min and then the column was washed with 240 mL of the loading buffer. The column was developed for 500 minutes at a flow rate of 2.5 mL/min at ambient temperature (23°) using a linear gradient of N$_\alpha$-acetylhistidine (1→100 mM). The eluate from the column was continuously monitored at 280 nm (0.2-2.0 AUFS) using a Kratos Model 757 spectrometer equipped with a 3 mm path-length cell. Fractions (25 mL) were collected using a Gilson Model 202 fraction collector. After the run was completed, the column was stripped with 50 mM Na$_2$H$_2$EDTA (pH=7.0) and then 50 mM NaOH. The column was ready for regeneration after washing with 100 mM NaCl (240 mL), loading buffer (240 mL) and finally 100 mM NaCl (240 mL). The fractions containing the somatotropin were collected and combined to yield 250 mL solution which contained 1.7 mg/mL protein. Typical analyses by analytical reverse phase HPLC (Vydac C18 column, H$_2$O/CH$_3$CN+0.1% CF$_3$CO$_2$H) of HIS$_{15}$-avbST at this stage showed the following (column A).

| Protein | A | B |
|---|---|---|
| Somatotropin monomer + isoforms | 96.6% | 98.2% |
| Somatotropin-related oligomer | 2.5% | 1.5% |
| Extraneous protein | 0.9% | 0.3% |

Sacrificing the back 15-20% of the somatotropin peak reduced the oligomer content to 1.0-1.5%. Concentrating the purified somatotropin and reloading it onto the same column (cleaned and regenerated) yielded slightly purer product (column B above) with 94% recovery.

Variations on this elution protocol were used. In our early experiments, Pharmacia Chelating Sepharose 6B was used; this gel was difficult to clean and flow rates were restricted. For larger column columns (0.5-2.0 L), we also used Pharmacia Chelating Sepharose Fast Flow. Although the chromatographic resolution was reduced somewhat, we sometimes found it convenient to use imidazole (0.5→45 mM) as the release buffer or to use 1.0M NaCl instead of 0.5M NaCl. The stronger binding variants, His$_{26}$His$_{30}$-avbST and HIS$_{11}$His$_{15}$-avbST, were more easily purified using imidazole (100 mM) as the release agent.

Ultrafiltration, Concentration and Lyophilization

The purified somatotropin solution (250-500 mL) was concentrated to 30-40 mL in volume using a 400 mL stirred Amicon ultrafiltration cell equipped with a YM10 membrane. If the metal-affinity column was used, 40 mg solid Na$_2$H$_2$EDTA·2H$_2$O was dissolved in the protein pool prior to concentration. Using 5 mM Na$_2$CO$_3$ (pH=10.0), the protein solution was diluted to 400 mL in volume and then reconcentrated to 30-40 mL under N$_2$ pressure. Three more cycles of dilution and reconcentration were carried out, yielding about 30 mL of purified somatotropin in carbonate buffer. The liquid was placed in a lyophilization flask along with enough water to increase the volume to 100 mL. The solution was frozen and placed on a Virtis Lyophilizer (Freezemobile 12) overnight. The resulting fluffy white solid was weighed and stored in a sealed container at $-20°$ C.

TABLE 1

BINDING OF PROTEINS TO IMMOBILIZED COPPER

| Protein[a] | Retention[e] (column volume) | Exposed Histidines |
|---|---|---|
| Ru$_{15}$Ser$_{169}$-pST[b] | 1.0 | 0 |
| Tuna Cytochrome C[b,c] | 0.9 | 0 |
| Ser$_{169}$-pST | 4.6 | 1 |
| His$_{25}$-mlbST | 4.8 | 2− |
| hST (human)[c] | 6.1 | 2 |
| pST | 6.2 | 2 |
| avbST | 6.3 | 2 |
| mlbST | 6.4 | 2 |
| His$_{165}$-avbST | 6.3 | 2 |
| His$_{132}$-mlbST | 7.4 | 2+ |
| His$_{132}$-avbST | 7.5 | 2+ |
| His$_{152}$His$_{156}$-avbST | 8.9 | 3 |
| His$_{94}$-mlbST | 9.5 | 3 |
| His$_{16}$-mlbST | 9.8 | 3 |
| His$_{149}$-mlbST | 9.9 | 3 |
| His$_{149}$-avbST | 9.8 | 3 |
| His$_{173}$-avbST | 17.3 | 3 (HH chelate + 1) |
| His$_{15}$-mlbST | 23.7 | 3 (HH chelate + 1) |
| His$_{15}$-avbST | 23.2 | 3 (HH chelate + 1) |
| His$_{15}$-pST | 23.5 | 3 (HH chelate + 1) |
| His$_{15}$Pro$_{133}$-avbST | 23.0 | 3 (HH chelate + 1) |
| His$_{11}$His$_{15}$-avbST[d] | 42.4 | 4 (tandem H$_3$ chelate + 1) |
| His$_{26}$His$_{30}$-avbST[d] | 49.9 | 4 (HH chelate + 2) |

[a]Numbering system is that of Seeburg et al. DNA. 2. p. 37 (1983); avbST is bovine Ala$_{-1}$Val$_{126}$-somatotropin. mlbST is bovine Met$_{-1}$Leu$_{126}$-somatotropin and pST is porcine Ala$_{-1}$somatotropin. Unless otherwise specified, the amino acid at the −1 position is the first residue in the protein.
[b]Nonbinding reference protein. His$_{15}$ is blocked by —Ru(NH$_3$)$_5^{3-}$ in Ru$_{15}$Ser$_{169}$-pST; for ruthenation procedure, see A.W. Axup et al. J. Amer. Chem. Soc., 110. p. 435. (1988).
[c]Purchased from Sigma Chemical Company.
[d]1 →200 mM linear gradient of N$_\alpha$-acetylhistidine over 1000 minutes. Imidazole is better release agent for these proteins.
[e]2.0 mg of protein applied to a copper-loaded 10 mL column (1.0 × 13.0 cm) of Pharmacia Chelating Sepharose 6B. Eluted with a linear gradient (1 →100 mM) of N$_\alpha$-acetylhistidine over 500 minutes at flow rate of 0.5 mL/min. Buffers also contained 1000 mM NaCl and 50 mM NaH$_2$PO$_4$, pH = 7.0.

EXAMPLE 2

VARIANT SOMATOMEDIN

This example illustrates application of the present invention to a protein, namely, somatomedin C, which does not contain an available metal-binding amino acid, wherein two metal-binding amino acids are engineered thereinto to effect a metal-chelating sequence. This example also illustrates application of the present invention to a protein wherein the 3-dimensional structure has not been determined.

Somatomedin C, or "insulin-like growth factor-1" as utilized herein refers to IGF1. It is contemplated that IGF2, as well as proinsulin and insulin, can be modified in substantially the same manner with substantially similar results. For example, Ala$_8$ and Asp$_{12}$, which are predicted according to the procedures set forth above to be located at an α-helical segment of IGF1, were both replaced with histidine according to the procedure set forth below. Enhanced affinity for the His$_8$His$_{12}$-IGF1 variant is shown in Table 3. The residue at position 16, rather than at position 8, can also be replaced with a histidine since the α-helical segment is predicted to extend to position 17.

with 0.1 ml each of water saturated phenol and of chloroform. The aqueous phase was removed, and 0.7 mL 95% ethanol was added to it and mixed.

Synthetic oligonucleotides were produced by phodiester chemistry using an Applied Biosystems DNA synthesizer. The sequences of these oligonucleotides is shown below:

```
#1  5' CATGGCAGGACCAGAAACTCTTTGCGGCCATGAACTTGTTCATGCTCTGCA 3'
#2  3'     CGTCCTGGTCTTTGAGAAACGCCGGTACTTGAACAAGTACGAG       5'
```

Choice of Bacterial Strains and Starting Plasmids

Strains used were JM101 (supE, thi, (lac-proAB), [F', traD36, proAB, lacIqZ M15]) (C. Yanisch-Perron, J. Vieira, J. Messing, Gene, 33, 103, [1985]) and BW313 (dut, ung, thi-1, relA, spoTl/F' lysA). (T. A. Kunkel, Proc. Natl. Acad. Sci., 82, 488, [1985]) Plasmid pMON2464 consists of the replicon of pBR327 (L. Covarrubias, L. Cervantes, A. Covar-rubias, X. Soberon, A. Blanco, Y. M. Kupersztoch-Portnoy, F. Bolivar, Gene, 13, 25, [1981]) into which an expression cassette has been inserted in place of a portion of the tetracycline gene. The promoter used is derived from the rec A gene of E. coli; the ribosome binding site used is from gene 10 of phage T7; (P. O. Olins, C. S. Devine, S. H. Rangwala, K. S. Kavka, Gene, 73, 227, [1988]) the gene encodes alanyl-IGF1 with histidine substitutions at positions 8 and 12. Downstream from the gene is a sequence of about 500 base pairs from pEMBL18. (L. Dente, C. Cesareni, R. Cortese, *Nucleic Acids Res.*, 11, [1983]). This sequence contains the origin of replication of the single stranded phage fl. In cells infected with phage R408, single stranded plasmid DNA is packaged into phage particles. In pMON2464, the EcoRI site and the PstI site in the sequence of the beta-lactamase gene have been eliminated by in vitro procedures.

Construction of Plasmids

Alanyl-IGF1 was found to be produced from pMON2446 at a level of about 10 percent of total cell protein. The protein could be recovered easily from insoluble inclusion bodies and could be refolded into its active conformation. The production of IGF1 variants containing metal binding sites was made by constructing alanylIGF1 variants which differed in coding sequence from pMON2446 only in the codons required to specify the amino acid changes.

Method A. The construction of pMON2464 which encodes alanyl-IGF1 with histidine replacements at position 8 and 12 is now described. The DNA between the NcoI and PstI sites in pMON2363 was replaced with complementary synthetic oligomers which encode the N terminal 16 codons of the alanyl-IGF1 gene. The DNA of pMON2363 was used because it contains the gene for an IGF1 variant which has nine more bases of DNA between the NcoI and PstI sites than does pMON2446. Substitution of the DNA of pMON2363 between the NcoI and PstI sites with synthetic DNA which is of shorter length permitted the identification of recombinant plasmids which encode the desired alanyl-IGF1 variants. One microgram of the DNA of pMON2363 was treated with the restriction enzymes NcoI and PstI at 37° C. for at least 2 hours in the following buffer: 10 mM Tris.HCl (pH 7.5), 5 mM MgCl$_2$, 150 mM NaCl. To the restriction enzyme reaction mixture NaOAc was added to a final concentration of 300 mM in a final volume of 0.3 mL. The sample was extracted with 0.1 ml each of water saturated phenol and of chloroform. The aqueous phase was removed, and 0.7 mL 95% ethanol was added to it and mixed.

These oligonucleotides were passed through a duPont Nensorb column to remove salts. Purification of the oligonucleotides from a polyacrylamide gel was not necessary. Approximately 1000 picomoles of the oligonucleotides were resuspended in water. One hundred picomoles of each of the complementary oligonucleotides were mixed in a volume of 50 microliters in the following buffer: 6.6 mM Tris (pH 7.4), 6.6 mM MgCl$_2$, 6.6 mM NaCl and 5 mM dithiothreitol. The sample was placed in boiling water which was allowed to cool to room temperature to permit annealing of the oligonucleotides. Ten picomoles of the annealed oligonucleotide mixture was added to an aliquot of one half of the NcoI and PstI treated pMON2363 DNA in ethanol. Both this sample and the other half of the pMON2363 DNA were chilled, and the DNA was collected by precipitation. The dried pellets were resuspended in 20 microliters of ligation buffer: 25 mM Tris (pH 8.0), 10 mM MgCl$_2$, 0.2 mM spermidine, 1 mM dithiothreitol and 1 mM ATP. To this, 10 units of T4 D ligase was added, and the reaction mixture was incubated overnight at 15° C.

Method B. Single stranded DNA of pMON2464 was isolated. A culture of E. coli strain BW313 harboring pMON2464 was grown in 2XYT medium (16 grams tryptone, 10 grams yeast extract, 5 grams NaCl per liter) with the addition of 200 micrograms per milliliter of ampicillin. At a Klett value of 110, phage R408 (Stratagene) was added to a final concentration of 10(9) phage per milliliter. At the same time uridine was added to a final concentration of 0.25 microgram per mL. The culture was allowed to grow with shaking at 37° C. overnight. Four to six milliliters of culture were subjected to centrifugation to remove cells. To the supernatants were added one fourth volume of phage precipitation buffer (2.5 M NaCl, 10% w/v polyethylene glycol M6000, 0.15 mM EDTA (pH 7.0), 10 micrograms per milliliter pancreatic RNase). These samples were kept at 4° C. overnight. The phage from one milliliter of culture supernatant were collected by centrifugation and resuspended in 50 microliters protease K digestion buffer (10 mM Tris.HCl pH 7.4, 0.1 mM EDTA, 0.2% sarkosyl and 0.05 mg/mL protease K). The samples were incubated at 65° C. for one hour and then chilled on ice. NaCl was added to a final concentration of 400 mM. The samples were vortexed in the presence of one half volume each of water saturated phenol and chloroform. The aqueous phase was removed and the nucleic acid was precipitated with two volumes of cold ethanol. The dried pellets were resuspended in 10 microliters of water per four milliliters of original culture supernatant.

The single stranded DNA was derived predominantly from the plasmid rather than from the phage R408. A low level of uracil incorporation results from the growth of the plasmid in strain BW313. This permitted a selection in favor of an in vitro synthesized complementary strand which contains no uracil. To prime synthesis of this strand, a synthetic DNA oligonucleotide was used. The sequence of this oligonucleotide (5'GCAAACGTGCTGCAGAGCATGAACAAG 3') differs from the complement of the sequence of the single stranded template at the position of codon 16 of the IGF1 gene. The sequence of the oligonucleotide specifies histidine, whereas the template specifies phenylalanine at that position.

Fifty picomoles of this oligonucleotide was treated with polynucleotide kinase in the presence of 25 mM Tris (pH 8.0), 10 mM $MgCl_2$, 0.2 mM spermidine, 1 mM dithiothreitol and 1 mM ATP for 30 minutes at 37° C. and then 5 minutes at 65° C. Ten picomoles of the oligonucleotide were mixed with 4 microliters of the template prepared as described above. These were brought to a final volume of 10 microliters in Hin buffer: 6.6 mM Tris (pH 7.4), 6.6 mM $MgCl_2$, 6.6 mM NaCl, 5 mM dithiothreitol. Tubes containing the samples were suspended in a beaker of water which was brought to a boil and allowed to cool to room temperature. This permitted the annealing of the oligonucleotide to the template. To the cooled mixture was added nine microliters of NTP mix: Hin buffer, 1 mM of each of the four deoxynucleotide triphosphates, and 1 mM rATP. To these samples were added 3 units each of T4 DNA ligase and the Klenow fragment of DNA polymerase I of E. coli. Both of these enzymes were obtained from Boehringer Mannheim. The samples were then incubated at 15° C. overnight.

Introduction of Plasmid into Cells and Cell Screening

A culture of E. coli JM101 cells were made competent to take exogenous DNA. The cells were collected from a culture growing at 37° C. in LB medium. They were then resuspended in ½ culture volume with 50 mM $CaCl_2$. After storage on ice for 30 minutes, the cells were collected by centrifugation, and the cell pellets were resuspended in 1/10 culture volume in 50 mM $CaCl_2$. After one half hour incubation at 4° C., the samples were incubated at 42° C. for one minute. One milliliter of L broth was added, and then the samples were incubated at 37° C. for 2 hours. The cells were collected by centrifugation and spread on agar plates containing 200 mg/mL of ampicillin. Colonies which grew after overnight incubation at 37° C. were picked into liquid broth also containing 200 mg/mL ampicillin. Plasmid DNA was isolated from the cells in these cultures by standard methods and subject to analysis by polyacrylamide gel electrophoresis of the DNA which had been treated with restriction endonucleases. Those plasmid DNAs which were found to contain DNA restriction fragments whose size indicated the presence of the synthetic DNA in place of the parental DNA were chosen as candidates for the desired recombinant. The DNA of these plasmids was subjected to DNA sequence analysis by standard methods to confirm the presence of the desired sequence between the NcoI and PstI restriction sites.

Bacterial Fermentation

E. coli strain W3110 II-4 harboring plasmid pMON2464 was used to produce a variant of alanyl-IGF1 which contains histidine substitutions at positions 8 and 12. A transformant of W3110 II-4 which harbors the plasmid pMON2464 was used to start an overnight culture in L broth containing 200 mg/mL of ampicillin. This was used to inoculate a fermentor culture. The growth medium contained the following: KOH, $H_3PO_4$, $(NH_4)_2SO_4$, $MgSO_4$, trace metals and Alimet. Liquid dextrose was used as carbon source and the residual dextrose concentration in the fermentor was maintained between 0.05% and 0.25% using a concentrated dextrose feed strategy. No antibiotic was added to the fermentor. Fermentation run parameters were as follows: 37° C., 100 rpm agitation, air sparge rate of 10 liters per minute, 5 psi back pressure and pH setpoint controlled at 7.0 with ammonium hydroxide. When the culture had grown to optical density (550 nm) of 20, the temperature was shifted from 37° C. to 33° C. and maintained for the duration of the run. When the culture reached an optical density (550 nm) of 42, nalidixic acid was added to a final concentration of 25 ppm to induce expression of the IGF1 variant gene from the rec A promoter on pMON2464. The cells were 20 then harvested, frozen and stored at −80° C.

Cell Lysis and Isolation of Inclusion Bodies

After thawing an appropriate amount of frozen cell paste at 5° C., 110g of the cell paste was carefully suspended in 480 mL cold water using an Ultra Turrax stirrer. The chilled cell suspension was passed 4 times through a pre-cooled Manton Gaulin homogenizer set at 6000–8000 psi pressure. The resulting suspension of lysed cells was subjected to ultracentrifugation at 50,000 ×g (25,000 rpm in 45TI rotor) for 35 minutes using a Beckman Model L8 centrifuge. The clear supernatant liquid was poured off, and the remaining brownish pellet was vigorously washed with a small stream of water in order to remove the top slimy layer of unwanted cell debris. The pellet was resuspended in water and subjected a second time to ultracentrifugation and washing. The remaining material was mechanically scraped out of the centrifuge tubes and combined to yield 2.6 g of damp inclusion bodies which were stored at −80° C. for future use.

Oxidation and Folding of IGF1

Method A. A 1.3 g mass of inclusion bodies was suspended in 80 mL cold buffer (6 M urea + 25 mM Tris, pH=9.0) using an Ultra Turrax stirrer. Dithiothreitol (120 mg) was added to the mixture in order to reduce and solubilize the inclusion bodies. This mixture was stirred at 5°–10° C. for 10 minutes, and then 160 mL of cold Tris buffer (25 mM, pH=9.0) was added. The pH of this mixture was rapidly raised to 11.0 by dropwise addition of 2.5 M NaOH. The mixture was stirred for about 1 minute and then the pH was rapidly reduced to 9.5 by dropwise addition of 6 M HCl. This solution was vigorously stirred in an open container at 5° C. for 16 hours in order to complete the folding process. In order to remove residual insolubles, the refolded mixture was subjected to ultracentrifugation at 50,000 ×g (25,000 rpm in Beckman 45TI rotor). The clear pale yellow supernatant liquid was decanted off and then prepared for purification by adding 1.4 g NaCl and adjusting pH to 8.5.

Method B. A 2.6 g mass of inclusion bodies was suspended in 100 mL cold buffer (6 M urea + 25 mM $Na_3$-$BO_3$, pH=9.5) using an Ultra Turrax stirrer, Dithiothreitol (150 mg) was added to the mixture in order to reduce and solubilize the inclusion bodies. This mixture was stirred at 10° C. until most of the inclusion bodies had dissolved (~10 minutes), and then 1100 mL of cold borate buffer (25 mM, pH=9.5) was added. The pH of the mixture was checked to make sure that it was 9.5.

This solution was vigorously stirred in an open container at 5° C. until the oxidation was complete (10-48 hours). Sodium chloride (7.0 g) was dissolved in the refold mixture followed by dropwise addition of glacial acetic acid until the pH was 4.5. The mixture was then subjected to ultracentrifugation at 50,000 ×g (25,000 rpm in Beckman 45TI rotor . The clear supernatant liquid was decanted off, the pH was adjusted to 8.5 using 2 M NaOH, and then the protein solution was stored at 4° C. awaiting further purification.

Preparation of Functionalized Resin

Trisacryl GF2000M was repeatedly washed with distilled water to remove all buffers and preservatives and then dried by suction. About 100 g (~100 mL) of this slightly damp matrix was suspended in a solution containing 80 mL diglyme and 100 mL freshly prepared 1.4 M NaOH solution. Finally, 100 mL diethyleneglycol diglycidylether was added, and the mixture was gently stirred at 35° C. for 16 hours. Purified diethyleneglycol diglycidylether was prepared by a literature method. (X. Gu, I. Ikeda, M. Okahara, Synthesis, 649,[1985]) The activated matrix was washed with diglyme/$H_2O$ (50/50) and then repeatedly washed with distilled water to remove the excess epoxide and base. The washed, suction-dried matrix was shown to have 70 micromoles active epoxide groups per mL resin. The activated resin was stored at 4° C. and generally used within 24 hours of preparation.

Immobilization of Chelate

The activated Triascryl was washed with distilled water and dried by suction. About 100 g (~100 mL) of this activated gel was suspended in 100 mL 1.0 M $Na_2NH(CH_2CO_2)_2$ solution, which was adjusted to pH=10.5-11.0. This mixture was gently stirred at 65° C. for 24 hours and then repeatedly washed with distilled water to remove excess ligand. The functionalized resin was stored in ethanol/water (25/75 v/v) at 4° until ready for use. Titration with thiosulfate showed the absence of epoxide groups, so capping with ethanolamine was deemed unnecessary. Ten milliliters of suction-dried gel was saturated with excess 50 mM $Cu(ClO_4)_2$ and then carefully washed with 00 mL distilled water, 100 mL 50 mM imidazole (pH=7.0) and finally 100 mL $H_2O$. Then the bound copper was removed with an excess of 50 mM $Na_2H_2EDTA$ (pH=7.0). Using standardized copper-EDTA solutions for comparison, the total copper content was photometrically determined to be 0.43 millimoles.

Elution Protocol for Metal Affinity Column

A glass column (1.6×13 cm, 26 mL) was packed with carefully washed IDA-Trisacryl gel and then charged with 130 mL 50 mM $Cu(ClO_4)_2$ (pH 4.5). The functionalized gel nearly quantitatively absorbed the copper ions. This copper column was washed with 100 mM NaCl, and then it was equilibrated with the release buffer (50 mM imidazole, 500 mM NaCl, 50 mM $NaH_2PO_4$, pH=7.0) and finally equilibrated wtih the loading buffer (0.5 mM imidazole, 500 mM NaCl, 50 mM $NaH_2PO_4$, pH=7.0). The clarified crude refold mixture (~1200 mL) was adjusted to pH=8.5 and then pumped onto the column at 4.0 mL/min; the column was then washed with 80 mL of the loading buffer. The column was developed for 500 minutes at a flow rate of 1.3 mL/min at ambient temperature (23°) using a linear gradient of imidazole (0.5→50 mM). The eluate from the column was continuously monitored at 280 nm (0.05-0.5 AUFS) using a Kratos Model 757 spectrometer equipped with a 3 mm path-length cell. Fractions (13 mL) were collected using a Gilson Model 202 fraction collector. After the run was completed, the column was stripped with 50 mM $Na_2H_2EDTA$ (pH 7.0) and then 50 mM NaOH. The column was ready for regeneration after washing with 100 mM NaCl (240 mL), loading buffer (240 mL) and finally 100 mM NaCl (240 mL). Two strong binding protein peaks eluted off the copper column. The fractions containing the second peak were collected and combined to yield 80-100 mL solution which contained 30-40 mg protein. A typical analysis by analytical reverse phase HPLC (4.6×250 mm, Brownlee $C_8$ Aquapore column, $H_2O/CH_3CN+0.1\%$ $CF_3CO_2H$, 210 nM) of $A_{-1}H_8H_{12}$-IGF1 at this stage gave the following results.

| Protein | Analysis |
|---|---|
| IGF1 | 73% |
| IGF1 monomeric isoform | 16% |
| IGF1-related oligomer | 10% |
| Extraneous protein | 1% |

In addition to our Trisacryl gel, Pharmacia Chelating Sepharose Fast Flow was used with acceptably good results.

Elution Protocol for Reverse Phase HPLC

The purified somatomedin solution (~100 mL/~36 mg total protein) was concentrated to 1.5 mg/mL protein concentration using a 100 mL stirred Amicon ultrafiltration cell equipped with a YM2 membrane. Part of the concentrated sample (12 mL) was filtered 0.2 μm) prior to injection onto the reverse phase column, and the remainder of the sample was frozen for future use. The column used was an Aquapore R-300 $C_8$ reverse phase column (7.0×250 mm) distributed by Brownlee Labs. The column was equilibrated with a 0/90 mixture of acetonitrile-water (0.1% $CF_3CO_2H$), and then the protein solution was injected onto it. The column was developed for 50 minutes at a flow rate of 3.0 mL/min. at ambient temperature using a linear acetonitrile gradient until the final solvent composition was 60/40 acetonitrile-water (0.1% $CF_3CO_2H$). The eluate from the column was continuously monitored at 280 nm (0.2-2.0 AUFS) using a Kratos Model 757 spectrometer equipped with an 8 mm cell. Fractions (0.9 mL) were collected using a Gilson Model 202 fraction collector. Properly folded $A_{-1}H_8H_{12}$-IGF1 eluted off the column at 22 minutes (~32% MeCN), its companion isoform came off at 25 minutes (~35% MeCN) and several oligomer peaks came off in the range 27-35 minutes. The relevant fractions containing the IGFI were analyzed using analytical reverse phase HPLC. Eight fractions containing the main peak were pooled and shown to contain 13 mg at 98+% purity. Three fractions containing the isoform were pooled and shown to contain 1.6 mg at 95% purity. The column was cleaned by washing with 90/10 MeCN-$H_2O$ and then reequilibrated with the starting buffer 10/90 MeCN-$H_2O$ (0.1% $CF_3CO_2H$). The remaining sample was thawed and similarly purified using the same procedure.

Lyophilization

Requisite volumes (0.1-1.5 mL) of the purified IGF1 solutions were pipeted into 2 mL Eppendorf tubes and placed in a Savant Vacuum Concentrator (Speedvac, SVC 200H) in order to remove the solvents (H₂O, CH₃CN, CF₃CO₂H). The purified proteins were obtained as fluffy white solids and stored at −80° C. The total yield of purified $A_{-1}H_8H_{12}$-IGF1 was 26.4 mg; 3.2 mg of the companion isoform was also obtained.

S-Sulfonation Procedure

About 1.5 mg $A_{-1}H_8H_{12}$-IGF1 (misfolded or properly folded) was d in 1.5 mL sulfonation buffer which contained 125 mM $Na_2SO_3$, 25 mM $Na_2S_4O_6 \cdot 2H_2O'$ 25 mM $H_3BO_3$ and 6M urea (pH 8.5). The reaction was allowed to proceed for 3 hours at 25° C. or 12 hours at 5° C. after which the reaction mixture was filtered (0.2 μ) and injected onto the reverse phase HPLC column (see above). Despite the formation of six additional negative charges, the protein was more hydrophobic and eluted from the column in 29 minutes (~39% MeCN). The fractions containing the product were handled in the same manner as the native protein to yield 1.3 mg pure $A_{-1}H_8H_{12}IGF1(SO_3)_6$.

Modeling Metal Chelating Sites in Proteins

The simultaneous interaction of two or more metal-binding sites of a single multidentate ligand to a single metal or single cluster of rigidly attached metals is called metal chelation. It is known that properly designed chelates bind stronger to a particular metal than analogous non-chelating ligands. (A. E. Martell, R. M. Smith, Critical Stability Constants; Plenum Press: New York, 4 vols.[1975]) Properly designed means (1) that the chemical nature of the donor atoms in the ligands are matched to the particular metal ion or metal complex; (2) that the two or more metal-binding atoms easily satisfy the specific geometric requirements of the metal; (3) that the chelating form of the ligand is conformationally constrained (relatively inflexible, rigid).

Of the natural amino acids, only the side chains of cysteine, histidine, aspartate and glutamate have significant binding strength in aqueous solutions for divalent first row transition metals at neutral pH. (A. E. Martell, R. M. Smith, Critical Stability Constants; Plenum Press: New York, 4 vols. [1975])

*cys > his > > asp, glu > other amino acids*

For a cis disposition of ligands binding to $Cu^{2+}$ (similarly for $VO^{2+}$, $Ni^{2+}$, and $Zn^{2+}$), X-ray crystallographic data for metal complexes show that typical copper-nitrogen bonding parameters are Cu-N=1.98-2.02 Å and N—Cu—N=80°-100°. (G. Nardin, L. Randaccio, R. P. Bonomo and E. Rizzarelli, J. Chem. Soc., Dalton Trans., 369, [1980]. A. Podder, J. K. Dattagupta, N. N. Saha and W. Saenger, Acta Cryst., B35, 53 [1979]). X-ray crystallographic data for proteins show three commonly observed secondary structural features: α-helixes, β-strands and turns. These structured regions at least partially fulfill the requirement of conformational constraint. Typical conformational values for α-helices ($\phi = -57°$, $\psi = -47°$, $\omega = 180°$), (S. Arnott, A. J. Wonacott, J. Mol. Biol., 21, 371, [1966]). T. Blundell, D. Barlow, N. Borkatakoti, J. Thornton, Nature, 306, 281, [1983]) β-strands ($\phi = -139°$, $\psi = +135°$, $\omega = 180°$), (C. Chothis, J. Mol. Biol., 75, 295, [1973]) and β-hairpin turns (Type I', Type II') (B. L. Sibanda, J. M. Thornton, Nature, 316, 170, [1985]) were used. Geometric searches of energetically acceptable side-chain conformations (J. W. Ponder, F. M. Richards, J. Mol. Biol., 193, 775, [1987]) for histidine and aspartate residues were carried out in order to find which amino acid sequences coupled with corresponding secondary structures could provide a bidentate chelating site for $Cu^{2+}$ with the above distance and angular constraints. Only short range chelating interactions were considered; i.e., the number of intervening residues between the binding residues was 0 to 4. The results of the calculations are shown in the following table; (+) shows when chelation is possible, and (−) shows when chelation cannot occur. The nature of the intervening residues ("X") is relatively unimportant. The modeling showed that the steric size, the hydropathicity and the charge of the sidechains of these residues play only minor or secondary roles in determining the strength of the metal-chelating peptide interactions.

| Sequence | α-Helix | β-Strand | β-Hairpin Turn |
|---|---|---|---|
| HH | − | + | − |
| HxH | − | − | − |
| HxxH | − | − | + |
| HxxxH | + | − | − |
| HxxxxH | − | − | − |
| DH | − | − | − |
| DxH | − | + | − |
| DxxH | − | − | + |
| DxxxH | + | − | − |
| DxxxxH | − | − | − |
| HD | − | − | − |
| HxD | − | + | − |
| HxxD | − | − | + |
| HxxxD | + | − | − |
| HxxxxD | − | − | − |

Locating Secondary Structure

In the absence of more reliable structural information, regions containing significant secondary structure were determined from amino acid sequence information using the prediction algorithms of Nagano (K. Nagano, J. Mol. Biol., 109, 251, [1977]), Chou (P. Y. Chou, G. D. Fasman, Adv. Enzymol., 47, 45, [1978]), Garnier (J. Garnier, D. J. Osguthorpe, B. Robson, J. Mol. Biol., 120, 97, [1978]) and Wako (H. Wako, N. Waito, H. A. Scheraga, J. Protein Chem., 2, 221, [1983]); a fifth method using homologies to sequences in known structures was also used. These five predictive methods were applied to each protein from a series of aligned, homologous proteins. Only when there was substantial agreement between all predictions was a joint prediction considered to be reliable. Table 2 below shows the joint prediction of proinsulin from eight mammalian species (human, pig, guinea pig, rat, mouse, horse, cow, dog) and the joint prediction of insulin-like growth factor-1 from four mammalian species (human, cow, rat, mouse . The composite predictions for proinsulin and IGF1 shows that no β-structure is reliably predicted. However, two regions containing turns (19-23, 39-42) are moderately predicted, and one helical region (8-17) is strongly predicted.

TABLE 2

STRUCTURE PREDICTIONS FOR IGF1

```
                           1                  2
Numbering              1 2 3 4 5 6 7 8 9 0 1 2 3 4 5 6 7 8 9 0 1 2 3 4 5 6
Proinsulin Prediction¹           t t CCh HHHHHHHHHh t t t t t     t t h h h h h h Ct t t
Human Proinsulin                 FVNQHLCGS HL VE AL Y L V CGERGFFYTP K T R R E A E DL Q V G Q
Human IGF1                       GP ETLCGA EL VDAL Q F V CGDRGFYFN — — — — — — — — — — — — —
IGF1 Prediction²                          h HH HH Hh   b b     Ct t t
Composite Prediction³                     h HH HH HH Hh h   t t t t t
Exposure⁴                                 + O – O + O – + + –

2   3                4                5                6               7
Numbering              7 8 9 0 1 2 3 4 5 6 7 8    9 0    1 2 3 4 5 6 7 8 9 0 1 2 3 4 5 6 7 8 9 0 1 2 3 4 5 6 7 8 9 0
PI Predict             C C C C C C C C    h h h h h          t t      CCt t   bb bbb      C C
Hu-PI                  V E L G G G P G A G S L Q P L   A L E G S    L Q K R G I V E Q C C T S I C S   L Y Q L E N Y C N
Hu-IGF1                — — K P T G Y G S S S R R A — — — — — — P Q — T G I V E E C C F R S C D L R R L E M Y C A P L K P A K S A
IGF1 Predict           C C C C C C C C                       t t   t t bb      CCt t t t t t hh h
Comp Predict           C C C C C C C C                       t t
Exposure
```

¹Composite result of 40 predictions from 8 species (human, pig, guinea pig, rat, mouse, horse, cow, dog). H = strong helix prediction, h = moderate helix prediction. b = moderate β-structure prediction, t = moderate turn prediction. C = no helix nor β-structure.
²Composite result of 20 predictions from 4 species (human, cow, rat, mouse).
³Composite result of all individual proinsulin and IGF1 predictions.
⁴Exposed (+), buried (–), intermediate region (O).

Identifying Exposed Residues

Once regions of regular secondary structure have been identified, it is necessary to determine which residues in these regions are sufficiently exposed on the surface of the protein so that they could easily bind to metals. The periodicity of the hydropathy over the region of interest was used as a guide in finding the exposed residues. Although a number of hydropathy scales have been defined, the one most useful in the present application is the scale based on the degree to which a particular amino acid residue is buried or exposed as determined in proteins whose structures are determined by X-ray crystallography. (A. Kidera, Y. Konishi, M. Oka, T. Ooi, H. A. Scheraga, J. Protein Chem., 2, 221, [1983]).

α-Helix. For the entire helical region of interest, the hydropathic moment (direction and magnitude) was calculated using a pitch of 18 residues per 5 turns (100°/residue). If the hydropathic moment was sufficiently large (>|0.3| per residue), the residues were then classified into three equally populated categories; exposed (+), buried (–) and borderline (0).

The calulations for residues 8–17 in IGF1 and for the analogous region in proinsulin showed that residue 12 (asp/glu) had the best exposure to the solvent. Similarly, residues 8, 15, and 16 (ala/ser, gln/tyr, phe/leu) were exposed, and residues 10, 14 and 17 (leu/leu, leu/-leu, val/val) were buried. Residues 9, 11 and 13 were calculated to lie in an intermediate region, neither fully exposed nor completely buried; of these three residues, $E_9/H_9$ is more exposed, and $L_{11}/L_{11}$ and $A_{13}/A_{13}$ are more buried. With the exception of residue 16, the helix has good amphiphilic character. On the basis of those calculations, $H_8h_{12}$-IGF1 and $H_{12}H_{16}$-IGF1 were judged to contain the best metal binding sites. We overlooked several possible problems; (1) the proximity of residues 8 and 16 to the ends of the calculated helix, (2) the replacement of a hydrophobic residue ($phe_{16}$) by a hydrophilic histidine, (3) the possibility that residue 8 was part of a $G_7A_8$ turn.

β-Strand. For the entire β-strand region of interest, the hydropathic moment was calculated using a pitch of 2 residues per turn (180°/residue). This is an easy calculation for β-structures because each residue is either "up" or "down." In this case the residues were classified into two equally populated categories: exposed (+) and buried (–).

β-Hairpin Turn. Because these two-residue turns are super-secondary structures, there is little need for further calculations once the residues in the turn have been identified. The residues suited for metal chelation are the two residues on either side of the hairpin turn. These turns occur most frequently on exposed surfaces of proteins with the turn residues and immediately adjacent residues exposed.

Owing to the presence of neighboring cysteine, glycine or proline residues, neither predicted turn region (19–23, 39–42) in IGFI indicated a clearly defined, single 2-residue turn, and no good metal binding sites were judged to be present.

Biological Assay

The biological activity of the IGF1 variants was assayed by measuring enhancement of myoblast proliferation in vitro. Rat L6 myogenic cells (D. Yaffe, Proc. Natl. Acad. Sci., 61, 477, [1968]) were used in a cell proliferation assay. (C. E. Kotts, M. E. White, C. E. Allen, F. Martin, W. R. Dayton, J. Animal Sci., 64, 615, [1987]). Previous work has shown that native IGF1 will respond to this assay. (C. E. Kotts, C. A. Baile, Fed. Proc., 44, 484, [1985]). This assay was used with minor modifications which are briefly described.

Cells were plated onto 2 $cm^2$ wells (24-well plates, Corning) at 1000 cells/$cm^2$ in Dulbecco's Minimum Essential Medium (DMEM, Dibco Laboratories, Grand Island, N.Y.) containing 10% fetal bovine serum (FBS, Gibco). After 24 hrs, the test medium containing the variant IGF1 (0.1–50 nM) in DMEM plus 2% FBS was applied (1 mL/well). Stock solutions of fragments were prepared in 10 mM HCl at a concentration of 10 mg/mL. Fresh test medium was applied again 24 hours later. After an additional 48 hr, cell number was estimated by measuring the content of DNA on each well. DNA content was correlated with cell number using a standard curve consisting of known numbers of L6 cells as counted on a Coulter counter (Model ZM, Coulter Electronics, Hileah, Fla). Controls received DMEM containing 2% FBS and appropriate volumes of 10 mM HCl. Positive controls received various concentrations (0.1–50 nM) of recombinant human/bovine IGF1 (Monsanto Co. Lot S105, St. Louis, Mo.) in DMEM plus 2%

FBS. All incubations were carried out at 37° C., 10% $CO_2$ and 100% humidity. Results are presented as percent increase in cell number over controls (DMEM+2% FBS) within each assay and defined as stimulation. Intra-assay variation averaged 5.1% (±1.2%) and inter-assay variation was 22.2% among the experiments used in this study.

Single point assays at 0.1, 1 and 10 nM concentration of IGF1 showed the following activities:

|  | 0.1 nM | 1 nM | 10 nM |
|---|---|---|---|
| Native IGF1 | − | + | + |
| $A_{-1}H_8H_{12}$ IGF1 - misfolded | − | − | − |
| $A_{-1}H_8H_{12}$ IGF1 isoform - misfolded | − | − | − |
| $A_{-1}H_8H_{12}$ IGF1 | − | + | + |
| $A_{-1}H_8H_{12}$ IGF1 isoform | − | + | + |

A complete kinetic analysis of the concentration dependent rates of proliferation for two of the above proteins gave the following results:

| Protein | $K_m$ | $V_{max}$ |
|---|---|---|
| Native IGF1 | 2.9 nM | 168% |
| $A_{-1}H_8H_{12}$ IGF1 | 1.5 nM | 138% |

The values of effective $K_m$ are the same within experimental error (±factor of 2). The value of $V_{max}$ for the IGF1 variant shows good maximal activity, although it is somewhat lower than the native protein (±20% error).

oligomers, isoforms and misfolded monomers, as well as a variety of bacterial proteins, are found in the crude refold mixture. This example illustrates a method of purifying desired proteins directly from a crude refold mixture in one metal-affinity purification step.

Figure 2:
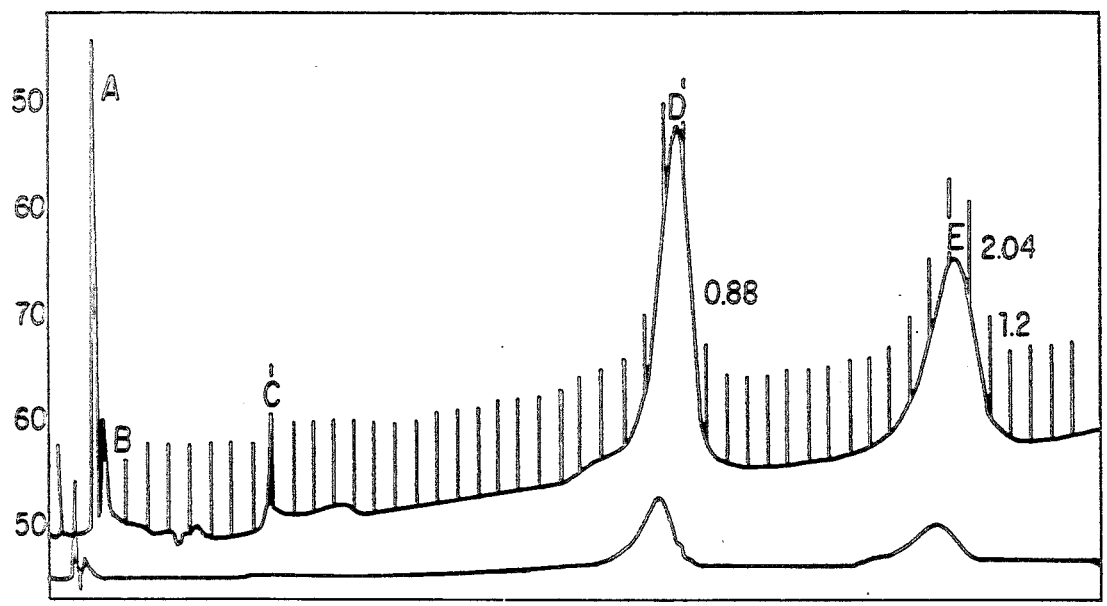
FIG. 2 illustrates the elution profile of a mixture of folded species of $A_{-1}H_8H_{12}$ insulin-like growth factor −1 (IGF1) modified according to the teachings of the present invention.

Because IGF1 has no endogenous histidine residues, two changes in the native protein were made and purified according to the procedure set forth in Example 2. The elution profile is shown in FIG. 1. In addition to IGF1 and a variety of bacterial proteins in the crude refold mixture, there is one major misfolded IGF1 monomer, IGF-related oligomers and at least one major IGF isoform. Upon purification of the crude refold mixture on a metal-affinity column, virtually all of the bacterial proteins were removed and most of the IGF oligomers were removed (residual oligomer content ≈4%-8%). Ordinarily it is difficult to separate the properly folded IGF1 from the misfolded IGF1; however, as a bonus, the metal clearly recognized the two differently folded forms and cleanly separated them. As illustrated in FIG. 2, the properly folded IGF1 binds strongest to the column. The misfolded IGF1 also binds reasonably well to the metal column, but the misfolding apparently distorts the helix which reduces its binding. The properly folded IGF1 isoform is easily separated by the metal column from the misfolded isomer but coelutes with the properly folded IGF1 itself. A second purification step (reverse phase HPLC or size exclusion chromatography) easily removed the residual IGF1 oligomer and also removed (reverse phase HPLC) the isoform.

TABLE 3

| BINDING OF IGF1 VARIANTS TO IMMOBILIZED COPPER | | |
|---|---|---|
| Protein | Retention[a] Volume | Exposed Histidines |
| IGF1 | 1.0 | 0 |
| $A_{-1}$-IGF1$(SO_3)_6$ | 1.0 | 0 |
| $A_{-1}$-IGF1 -misfolded | 1.0 | 0 |
| $A_{-1}$-IGF1 | 1.0 | 0 |
| $A_{-1}Q_9H_{12}$-IGF1$(SO_3)_6$ | 4.1 | 1 |
| $A_{-1}Q_9H_{12}$-IGF1 -misfolded | 5.6 | 1 |
| $A_{-1}Q_9H_{12}$-IGF1 | 5.5 | 1 |
| $A_{-1}H_{12}$-IGF$(SO_3)_6$ | 4.0 | 1 |
| $A_{-1}H_{12}$-IGF-misfolded | 5.6 | 1 |
| $A_{-1}H_{12}$-IGF | 5.7 | 1 |
| $A_{-1}D_8Q_9H_{12}$-IGF1$(SO_3)_6$ | 3.9 | 1 |
| $A_{-1}D_8Q_9H_{12}$-IGF1 -misfolded | 6.6 | 1 (distorted DH chelate) |
| $A_{-1}D_8Q_9H_{12}$-IGF1 | 7.3 | 1 (DH chelate) |
| $A_{-1}H_8Q_9$-IGF1$(SO_3)_6$ | 4.2 | 1 |
| $A_{-1}H_8Q_9$-IGF1 -misfolded | 6.8 | 1 (distorted HD chelate) |
| $A_{-1}H_8Q_9$-IGF1 | 7.6 | 1 (HD chelate) |
| $A_{-1}H_8H_{12}$-IGF1$(SO_3)_6$ | 8.4 | 2 |
| $A_{-1}H_8H_{12}$-IGF1-misfolded | 16.7 | 2 (distorted HH chelate) |
| $A_{-1}H_8H_{12}$-IGF1 | 21.0 | 2 (HH chelate) |
| $A_{-1}H_{12}H_{16}$-IGF1$(SO_3)_6$ | 8.3 | 2 |
| $A_{-1}H_{12}H_{16}$-IGF1-misfolded | 16.8 | 2 (distorted HH chelate) |
| $A_{-1}H_{12}H_{16}$-IGF1 | 18.9 | 2 (HH chelate) |
| $A_{-1}H_8H_{12}H_{16}$-IGF1$(SO_3)_6$ | 13.0 | 3 |
| $A_{-1}H_8H_{12}H_{16}$-IGF1 -misfolded | 32.5 | 3 (distorted $H_3$ tandem chelate) |
| $A_{-1}H_8H_{12}H_{16}$-IGF1 | 38.4 | 3 (tandem $H_3$ chelate) |

[a] 50 μg of protein applied to copper-loaded 3.9 mL column (8 × 78 mm) of Chelating 5 PW (Toyo Soda) eluted with linear gradient (1-128 mM) of $N_\alpha$-acetylhistidine over 160 minutes at flow rate of 0.98 mL/min; buffers also contained 500 mM NaCl and 50 mM $NaH_2PO_4$ (pH = 7.0). Units are column volumes.

EXAMPLE 3

Proteins produced by recombinant DNA technology in bacteria are commonly accumulated in insoluble refractile bodies in the cytoplasm of the host cell. To recover the proteins in their active form, renaturation is required. Renaturation entails solubilizing, folding and sometimes oxidizing the protein to its native configuration. As a result of such renaturation process, various

What is claimed is:

1. In a method for fractionating proteins or polypeptides utilizing immobilized-metal affinity chromatography wherein a protein or polypeptide is contacted with an immobilized-metal affinity matrix and selectively eluted and recovered, the improvement which comprises enhancing the affinity of the protein or polypeptide for the immobilized-metal by engineering within the terminii of said protein or polypeptide, prior to fractionation, a metal-chelating amino acid sequence represented by the formula: -A-$B_x$-$C_y$-$D_z$-E-wherein A and E are independently metal-binding amino acids selected from the group consisting of histidine and aspartate, B, C and D are amino acids, and x, y and z are independently integers from 0 to 3 depending on the secondary structure of the surface exposed portion of the protein or polypeptide molecule that includes the metal-chelating or sequence-containing site and the particular metal-binding amino acids present in such sequence, provided that the combination x+y+z and the secondary structure of the segment of the protein or polypeptide including said sequence affords a stereochemical arrangement of A and E adapted to form a chelate with the immobilized metal.

2. Method of claim 1 wherein A and E are both histidine and x+y+z equals 3, said sequence being engineered into said protein or polypeptide on a α-helical segment thereof.

3. Method of claim 2 wherein the protein is somatomedin C.

4. Method of claim 2 wherein the protein is somatotropin.

5. Variant protein comprising a protein having been modified to include within the terminii of said protein a metal-chelating amino acid sequence represented by the formula -A-$B_x$-$C_y$-$D_z$-E-wherein A and E are independently metal-binding amino acids, B, C and D are amino acids and x, y, and z are independently integers from 0 to 3, provided that x+y+z in combination with the secondary structure of the segment of the protein containing the metal-chelating sequence affords a stereochemical arrangement of A and E adapted to form a chelate with an immobilized metal.

6. Variant protein of claim 5 wherein A and E are both histidine and x+y+z is equal to 3, said sequence being engineered into said protein on an α-helical segment thereof.

7. Variant of claim 6 wherein said protein is somatotropin.

8. Variant somatotropin of claim 7 in which one amino acid residue is replaced with histidine, said residue being selected from the group consisting of the residues at position 15 and 173.

9. Variant of claim 8 wherein said somatotropin is bovine somatotropin.

10. Variant of claim 8 wherein said somatotropin is porcine somatotropin.

11. Variant of claim 6 wherein said protein is somatomedin C.

12. Variant somatomedin of claim 11 wherein $Ala_8$ and $Asp_{12}$ are both replaced with histidine.

13. Variant somatomedin of claim 11 wherein $Asp_{12}$ and $Phe_{16}$ are both replaced with histidine.

* * * * *